US00PP10867P

United States Patent [19]

Bull

[11] Patent Number: Plant 10,867

[45] Date of Patent: Apr. 27, 1999

[54] NEW GUINEA IMPATIENS PLANT NAMED 'TINA'

[76] Inventor: Norbert Bull, Gaertnersiedlung 2, Goennebek, Germany

[21] Appl. No.: 08/881,085

[22] Filed: Jun. 23, 1997

[51] Int. Cl.[6] ..... A01H 5/00

[52] U.S. Cl. ..... Plt./318

[58] Field of Search ..... Plt./87.6, 318

[56] References Cited

U.S. PATENT DOCUMENTS

| | | | |
|---|---|---|---|
| P.P. 8,360 | 8/1993 | Bull | Plt./87.6 |
| P.P. 8,368 | 9/1993 | Bull | Plt./87.6 |
| P.P. 8,601 | 2/1994 | Kientzler | Plt./87.6 |

OTHER PUBLICATIONS

GTITM UPOVROM Citation for 'Tina' as per NL PBR BLM0195, Jul. 16, 1994.

GTITM UPOVROM Citation for 'Tina' as per DE PBR IM 00295, Jun. 15, 1994.

*Primary Examiner*—Howard J. Locker
*Assistant Examiner*—Kent L. Bell
*Attorney, Agent, or Firm*—Foley & Lardner

[57] ABSTRACT

A new and distinct cultivar of New Guinea impatiens plant named 'Tina', characterized by its white-pink flower color, with purple eye and pink markings, medium sized flowers, dark green foliage with red veins, small plant habit with weak growth habit, and early to medium flowering response.

1 Drawing Sheet

The present invention comprises a new and distinct cultivar of New Guinea Impatiens, referred to by the cultivar name 'Tina'.

'Tina' is a product of a planned breeding program and was originated from a hybridization made by the inventor Norbert Bull in a controlled breeding program in Goennebek, Germany, in 1991. The female parent was a seedling designated No. 2 and the male parent was a seedling designated No. 3. Both parents are proprietary cultivars used in the breeding program.

'Tina' was discovered and selected as one flowering plant within the progeny of the stated cross by the inventor in Autumn 1991 in a controlled environment in Goennebek, Germany.

The first act of vegetative or asexual reproduction of 'Tina' was accomplished when cuttings were taken from the initial selection in Autumn 1992 in a controlled environment in Goennebek, by, or under the supervision of, Norbert Bull.

Horticultural examination of plants grown from cuttings of the clone initiated in Spring 1993 in Goennebek, Germany, and continuing thereafter, has demonstrated that the combination of characteristics as herein disclosed for 'Tina' are firmly fixed and are retained through successive generations of asexual reproduction.

'Tina' has not been observed under all possible environmental conditions. The phenotype may vary significantly with variations in environment such as temperature, light intensity and day length, without, however, any variation in genotype.

The following observations, measurements, and comparisons describe plants grown in Hillscheid, Federal Republic of Germany under greenhouse conditions which approximate those generally used in commercial practice.

The following traits have been repeatedly observed and are determined to be basic characteristics of 'Tina', which in combination distinguish this New Guinea Impatiens as a new and distinct cultivar:

1. White-pink flower color with purple colored eye and pink markings
2. Medium sized flowers
3. Dark green foliage with red veining
4. Small plant habit, weak growth
5. Early to medium flower response
6. Good resistance to powdery mildew Of the many commercial cultivars known to the present inventor, the most similar in comparison to 'Tina' are the commercial varieties 'Melanie', disclosed in U.S. Plant Pat. No. 8,368, and 'Tahiti', disclosed in U.S. Plant Pat. No. 8,601.

In comparison to 'Melanie', 'Tina' has a more distinct purple-pink eye, a somewhat lighter main flower color, a more compact growth habit, and better lasting quality.

In comparison to 'Tahiti', the flowers of 'Tina' are of similar color and size, but differently shaped, with flowers of 'Tina' being slightly zygomorph in contrast to the nearly round flowers of 'Tahiti'. 'Tina' also has more distinct markings, darker green foliage, and a less vigorous growth habit.

The accompanying photographic drawing shows typical flower and foliage characteristics of 'Tina', with colors being as true as possible with illustrations of this type.

In the following description color references are made to The Royal Horticultural Society Colour Chart.

The color values were determined indoors from flowers taken from plants grown in Hillscheid, Federal Republic of Germany, under greenhouse conditions which approximate those generally used in commercial practice.

The description is based on plants which were planted as rooted cuttings in 10 cm pots in early March and grown at 20° C. minimum temperature.

Classification:

*Botanical.*—A hybrid of the genus Impatiens.

*Commercial.*—New Guinea Impatiens cv. 'Tina'.

Plant

A. General appearance and form:

*Habit.*—Compact, low with medium width, self-branching, and growth is indeterminate, although weak after flowering begins.

*Height.*—11 cm (10-week-old plants).

*Width.*—25 cm.

*Internode length.*—Variable, between 35–50 mm.

*Stem color.*—Dark red.

*Flowering response.*—7 weeks after planting of rooted cuttings.

*Flowering season.*—Generally indeterminate, mainly from March to October, depending on light intensity.
*Lasting quality of the bloom.*—About four weeks.
*Propagation.*—Usually terminal tips for cuttings.
*Rooting.*—Color is R.H.S. 159 B-C; roots initiate in about 18 days at 22° C., from sticking to transplanting; no distinguishing rooting habit.

B. Foliage:
*Leaf arrangement.*—Primarily in whorls.
*Shape of leaf.*—Narrow elliptic, with acute base and a acuminate tip.
*Margin.*—Slightly serrated, ciliated.
*Leaf, length.*—About 120 mm.
*Leaf, width.*—35–38 mm.
*Main color of upper surface.*—Dark green, R.H.S. 139A.
*Veins on upper surface, color.*—Red at the base, and light pink or inconspicuous from the base to the tip of the leaf.
*Variegation on leaf.*—Absent.
*Main color of lower surface.*—Dark red, about R.H.S. 184B or lighter.
*Veins on lower surface, color.*—Dark red.
*Petiole, length.*—About 15 mm.
*Petiole, color.*—Dark red.

Inflorescence

A. Flower:
*Flower number per node.*—About 5–7, in various stages of development, usually one flower per leaf.
*Form of corolla.*—5 petals per flower.
*Shape.*—Slightly zygomorph, flat, borne well above the foliage.
*Average length.*—64 mm.
*Average width.*—57 mm.
*Color (general tonality from a distance of three meters).*—Light pink to white or "blush white".
*Petal number.*—Five (5).
*Petal shape.*—Heart-shaped, weakly lobed.
*Petal size.*—Upper, lower, and side petals are 25–35 mm in width; petals are 25–30 mm in length.
*Petal texture.*—Smooth, slightly glossy.
*Main color of upper surface.*—R.H.S. 62 C-D or lighter.
*Color of lower surface.*—R.H.S. 62 C-D.
*Eye zone.*—Distinct, purple R.H.S. 66B.
*Markings on upper petal and lines on other petals.*—Pink, about R.H.S. 66 C-D.
*Spur shape and size.*—Downwardly curved, about 55 mm in length.
*Pedicel, length.*—About 30–35 mm.
*Spur, color.*—R.H.S. 53D or lighter.
*Pedicel, color.*—Brownish, about R.H.S. 180 B.

Reproductive Organs

Androecium:
*Stamens.*—Five (5) in number, fused, upper surface color is mainly R.H.S. 66B.
*Anthers.*—Hooded, color is about R.H.S. 11 D.
*Pollen.*—Color is about R.H.S. 4 D.

Gynoecium:
*Stigma and style.*—Five (5) in number, very short, color is about R.H.S. 60 C.
*Ovary.*—Five (5) celled, 3–5 mm in length, surface color is R.H.S. 139 A.

I claim:

1. A new and distinct cultivar of New Guinea Impatiens plant named 'Tina', as illustrated and described.

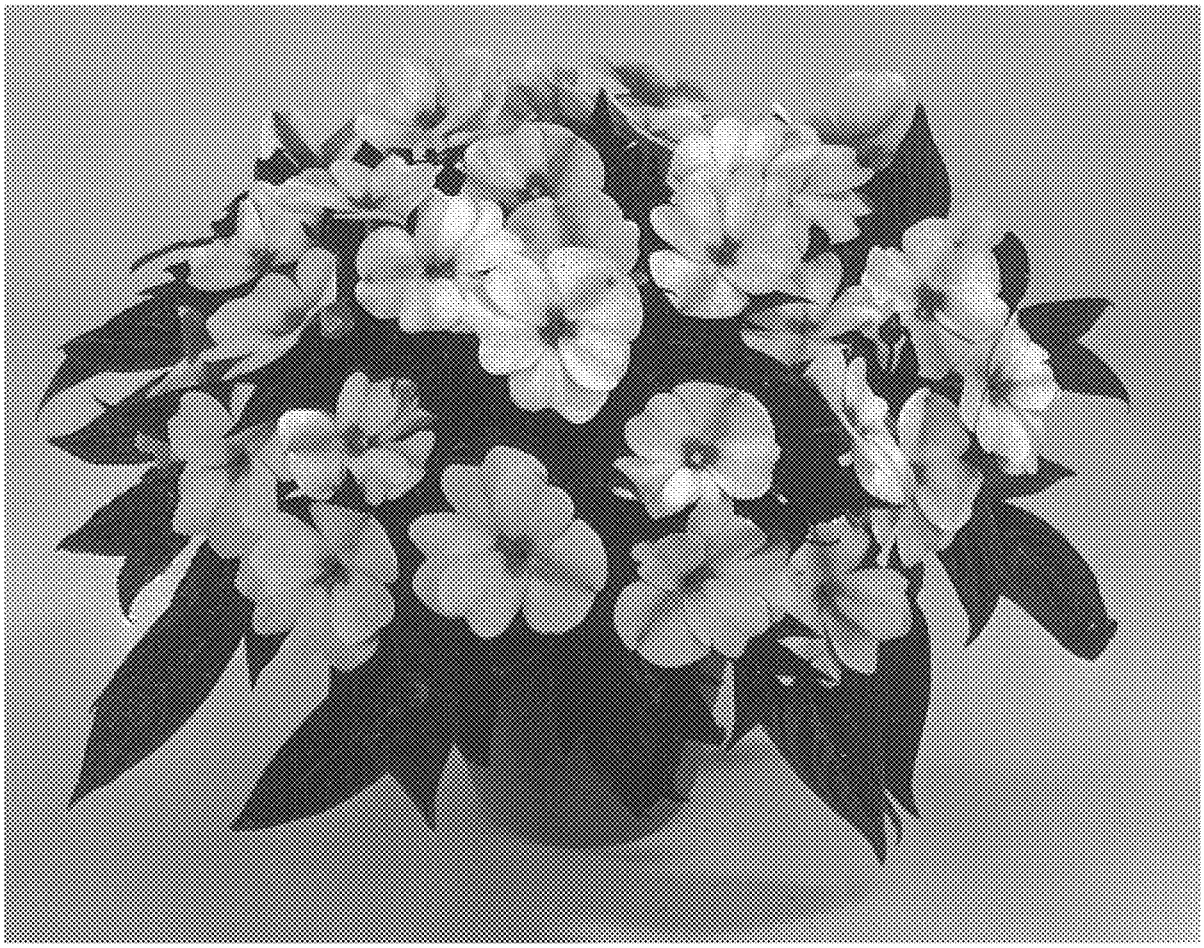

* * * * *